(12) United States Patent
Postaire et al.

(10) Patent No.: US 7,604,809 B2
(45) Date of Patent: Oct. 20, 2009

(54) **REINFORCING SYSTEMIC IMMUNE RESPONSES WITH *LACTOBACILLUS CASEI***

(75) Inventors: Eric Postaire, Vanves (FR); Benjamin Bonavida, Los Angeles, CA (US)

(73) Assignee: Compagnie Gervais Danone, Levallois-Perret (FR)

( * ) Notice: Subject to any disclaimer, the term of this patent is extended or adjusted under 35 U.S.C. 154(b) by 0 days.

(21) Appl. No.: 10/276,315

(22) PCT Filed: Apr. 27, 2001

(86) PCT No.: PCT/FR01/01310

§ 371 (c)(1),
(2), (4) Date: Sep. 10, 2003

(87) PCT Pub. No.: WO01/89541

PCT Pub. Date: Nov. 29, 2001

(65) Prior Publication Data

US 2004/0029127 A1      Feb. 12, 2004

(30) Foreign Application Priority Data

May 25, 2000    (FR) .................................. 00/06679

(51) Int. Cl.
   *A61K 39/145*    (2006.01)
   *A61K 39/38*    (2006.01)
   *A01K 63/00*    (2006.01)
(52) U.S. Cl. ............... 424/206.1; 424/184.1; 424/93.45
(58) Field of Classification Search ................... 426/46, 426/28, 36, 61, 71, 59, 44, 590, 594, 633; 424/93.45, 780, 438, 184.1; 435/252.1
   See application file for complete search history.

(56) References Cited

U.S. PATENT DOCUMENTS

| | | | | |
|---|---|---|---|---|
| 6,329,002 | B1 * | 12/2001 | Kim et al. | 426/71 |
| 6,572,854 | B1 * | 6/2003 | De Simone | 424/93.45 |
| 6,699,517 | B2 * | 3/2004 | Boufassa et al. | 426/46 |

FOREIGN PATENT DOCUMENTS

| | | |
|---|---|---|
| WO | 96 20607 | 7/1996 |
| WO | 99 10476 | 3/1999 |

OTHER PUBLICATIONS

Guerin-Danan, C. et al, Milk fermented with yogurt cultures and Lactobacillus casei compared with yogurt and gelled milk: influence on intestinal microflora in healthy infants, The American Journal of Clinical Nutrition, 1998, 67 (1) 111-117.*
Spencer, J., Probiotics: Potential for reducing the salmonella and campylobacter carrier state in poultry—Part I Salmonella, Confernece: Animal feed biotechnology research and scientific regulation international roundtable, 1992, 97-102.*
Perdigon, G. et al, Symposium: Probiotic bacteria for humans: clinical systems for evaluation of effectiveness, Journal of Dairy Science, 78: 1597-1606.*
Guerin-Danan, C. et al., (The American Journal of Clinical Nutrition, 1998, 67 (1) 111-117).*
(Viral Respiratory Infections, http://web.uct.ac.za/depts/mmi/jmoodie/vires2.html, pp. 1-8).*
eMedicine Consumer Health (www.emedicinehealth.com/fulltext/15361.htm, pp. 1-5).*
Yahui et al (Immunomodulatory function of lactic acid bacteria, Antonie van Leeuwenhoek, 1999; 76: 383-89).*
Actimel™ and DanActive™ (www.actimel.com, p. 1 of 2).*
(Wipe and Wash: Outwitting Germs in Child Care, Wisconsin Child Care Iimprovement Project, pp. 1-5).*
Actimel: a hard act to follow (www.new-nutrition.com/newspage/May0223a.htm.*
Freshney (Culture of Animal Cells, A Manual of Basic Technique, Alan R. Liss, Inc., 1983, New York, p. 4).*
Dermer (Bio/Technology, 1994, Vol. 12 p. 320).*
Susana Alvarez et al., "Specific Immunity Induction at the Mucosal Level by Viable Lactobacillus Casei: A Perspective for Oral Vaccine Development", Food and Agricultural Immunology, (1998) 10, pp. 79-87.
Gabriela Perdigon et al., "The Oral Administration of Lactic Acid Bacteria Increase the Mucosal Intestinal Immunity in Response to Enteropathogens", Journal of Food Protection, vol. 53, No. 5, pp. 404-410, Jun. 12, 1990.
Gabriela Perdigon et al., "Influence of the Use of Lactobacillus Casei as an Oral Adjuvant on the Levels of Secretory Immunoglobulin A During an Infection with Salmonella Typhimurium", Food & Agricultural Immunology (1993) 5, pp. 27-37.
H. Yasui et al.: "Immunomodulatory function of lactic acid bacteria" Antonie Van Leeuwenhoek, vol. 76, No. 1-4, pp. 383-389 Jul. 1999.
P.H. Pouwels et al.: "The potential of lactobacillus as a carrier for oral immunization" Journal of Biotechnology, vol. 44, No. 1, pp. 183-192 Jan. 26, 1996.
S. Uchida et al.: "Inhibition of animal virus plaque formation by culture filtrates of lactic acid bacteria" Kobe Journal of Medical Sciences, vol. 24, No. 2, pp. 91-98 1978.
T. Hori et al.: "Effect of intranasal administration of lactobacillus casei shirota on influenza virus infection of upper respiratory tract in mice" Clinical and Diagnostic Laboratory Immunology, vol. 8, No. 3, pp. 593-597, May 2, 2001.
G. Perdigón, et al., "Influence of the Oral Administration of Lactic Acid Bacteria on IgA Producing Cells Associated to Bronchus", International Journal of Immunopathology and Pharmacology, Vol. 12, No. 2, 1999, pp. 97-102.
S.K. Patidar, et al., "Methods for Assessing the Immunostimulating Properties of Dietary Lactobacilli—A Critical Appraisal", J. Food Sci. Technol., vol. 34, No. 3, 1997, pp. 181-194.

(Continued)

Primary Examiner—Robert B Mondesi
Assistant Examiner—Lakia J Tongue
(74) Attorney, Agent, or Firm—Oblon, Spivak, McClelland, Maier & Neustadt, L.L.P.

(57) ABSTRACT

The invention concerns the use of *Lactobacillus casei* in a composition for oral administration to enhance immunity specific to pathogenic micro-organisms. Said composition can in particular be a food or a food supplement.

12 Claims, 2 Drawing Sheets

OTHER PUBLICATIONS

G. Perdigón, et al., "Study of the Possible Mechanisms Involved in the Mucosal Immune System Activation by Lactic Acid Bacteria", J Dairy Sci, vol. 82, No. 6, 1999, pp. 1108-1114.

Vladimir Mihál, et al., "Protective Effect of Lactobacillus Acidophilus and Lactobacillus Casei on Encephalomyocarditis-virus-induced Disease in Mice", Food & Agricultural Immunology, Vo. 2, 1990, pp. 205-209.

* cited by examiner

REINFORCING SYSTEMIC IMMUNE RESPONSES WITH *LACTOBACILLUS CASEI*

This application is a national-stage filing under 35 U.S.C. 371 of PCT/FR 01/01310, filed Apr. 27, 2001. This application also claims priority to France 00/06679, filed May 25, 2000.

The invention relates to the use of lactic acid bacteria for potentiating the specific immune response against an infectious agent.

Lactic acid bacteria (LABs) are conventionally used to produce fermented food products, in particular dairy products.

The effects of lactic acid bacteria on the health were initially suggested by the studies of Metchnikoff (The prolongation of life. 1st ed. New York: GP Putman's Sons, 1908), and have since been the subject of many investigations.

It is now generally acknowledged that various lactic acid bacteria can exert a role which is beneficial to the health. These bacteria are also named "probiotics", a name which denotes living microorganisms which, when they are ingested in sufficient amount, exert a positive effect on the health, beyond the conventional nutritional effects. Probiotic bacteria have in particular been described among species belonging to the genera *Lactobacillus, Bifidobacterium, Streptococcus* and *Lactococcus*, commonly used in the dairy industry.

Probiotics are thought to intervene in particular at the level of the intestinal flora by impeding the development of pathogenic microorganisms, and/or by acting more directly on the immune system. It has, for example, been observed that ingestion of probiotic bacteria or fermented foods, such as yogurt, comprising these bacteria, leads to a decrease in pathogenic bacteria; in terms of the immune system, various effects have been reported: an activation of the cells involved in the specific or nonspecific immune response, such as lymphocytes and macrophages, an increase in the level of immunoglobulins and in particular of IgA; an increase in the level of immune system-activating cytokines, etc. (for review, cf. for example MEYDANI and HA (Am J Clin Nutr, 71, 861-7217, 2000).

Overall, the studies carried out on various probiotic lactic acid bacteria tend to conclude that some species, or at least some strains of these species, have immunostimulatory properties. On the other hand, the mechanism(s) underlying these properties, and the components of the immune system potentially involved, remain uncertain. It therefore appears to be necessary to elucidate these aspects, in particular in order to propose better targeted applications of the various species or strains of probiotic bacteria.

Several studies carried out in humans and animals suggest that bacteria of the species *L. casei* have a beneficial effect on the health, and in particular a positive effect on the immune system.

Thus, it has been shown in mice that ingestion of fermented milk containing the *L. casei* strain DN-114 001 increases resistance to infection with *Salmonella typhimurium* [PAUBERT-BRAQUET et al. Int J Immunother, 4:153, (1995)]; activation of macrophages and an increase in circulating IgAs have been observed simultaneously.

The strain DN-114 001 was deposited, on Dec. 30, 1994, with the CNCM (Collection Nationale de Cultures de Microorganismes) [National Collection of Microorganism Cultures] held by the Institut Pasteur, 25 rue du Docteur Roux, in Paris, under the number I-1518; this strain, and the combination thereof with yogurt ferments for preparing fermented dairy products, are described in PCT application WO 96/20607 in the name of COMPAGNIE GERVAIS DANONE.

Figure 1:
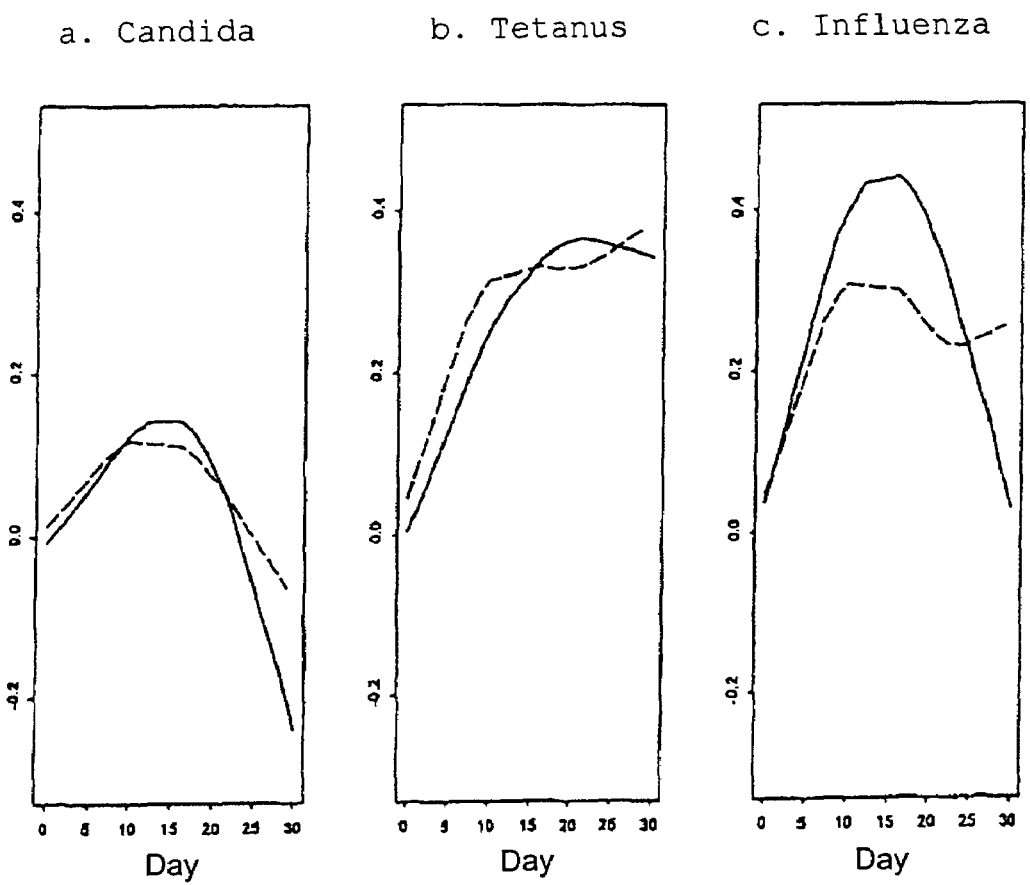
FIGS. 1*a, b,* and *c*, illustrate the variations in the proliferative response over time for *Candida*, tetanus or influenza antigens.

A recent study carried out in humans also reports that the consumption of fermented milk containing the *L. casei* strain DN-114 001 induces a reinforcement of resistance to *Salmonella typhimurium*. This effect is attributed to an action on nonspecific innate immunity [YOON et al., Int J Immunother; 15, 79-89 (1999)].

The inventors have investigated whether *L. casei* also has an action on adaptive immunity, which, unlike innate immunity, results in a specific immune response against a given pathogenic agent.

For this purpose, the inventors have studied the effect of *L. casei*, administered orally in vivo, on the ex vivo stimulation of T-cell proliferation in response to antigens representative of various types of common pathogenic agents: a bacterial antigen (tetanus); a fungal antigen (*candida*) and a viral antigen (influenza).

They have observed, for each of the antigens tested, that ingestion of *L. casei* leads to an increase in the proliferative capacity of T cells, and in particular of $CD3^{+-}$ sub-populations, in response to activation with said antigen. This effect manifests itself more particularly in the case of the influenza antigen.

A subject of the present invention is the use of a bacterial strain of the species *L. casei* for preparing a composition which can be administered orally to reinforce a specific systemic immune response against a pathogenic microorganism.

This reinforcement of the immune response ensues from an increase in the proliferative capacity of the T cells specific for the antigens of said pathogenic microorganism.

According to a preferred embodiment of the present invention, said microorganism is an aerially disseminated pathogen, in particular a pathogen of the respiratory tracts.

The pathogens concerned are especially bacteria or viruses; among the latter, mention will be made, for example, of rhinoviruses, respiratory syncytial virus (RSV), and myxoviruses (orthomyxoviruses such as the influenza viruses (influenza type A, B or C), or para-myxoviruses, and in particular para-influenzae).

In the context of the implementation of the present invention, said *L. casei* strain may be used alone or in combination with other lactic acid bacteria of the species *L. casei* or of other species. Advantageously, it may be used in combination with yogurt ferments, namely *Lactobacillus bulgaricus* and *Streptococcus thermophilus*.

It may be used in the form of whole bacteria, which may or may not be live, and also in the form of a bacterial lysate, or in the form of bacterial fractions.

Preferably, a composition prepared in the context of a use in accordance with the invention contains at least $10^5$, preferably at least $10^6$, generally between $1 \times 10^8$ and $1.5 \times 10^9$, *L. casei* cells per ml.

When *L. casei* is used in combination with yogurt ferments, said composition also advantageously comprises at least $10^7$, preferably between $2 \times 10^8$ and $1 \times 10^9$, *S. thermophilus* cells per ml, and at least $5 \times 10^5$, and preferably between $4 \times 10^6$ and $2 \times 10^7$, *L. bulgaricus* cells per ml.

An *L. casei* strain most particularly suitable for use in the present invention is the CNCM strain I-1518.

Compositions prepared in accordance with the invention may be administered in the form of foods or of food supplements. They may, for example, be dairy products, and in particular fermented dairy products comprising at least said *L. casei* strain, optionally combined with other lactic acid bacteria, for example with yogurt ferments.

Compositions prepared in accordance with the present invention can be used in the context of the prevention and treatment of pathological conditions of infectious origin, and in particular of viral origin, and in particular of the flu. Preferably, in order to obtain an optimal effect, they will be administered for at least one week, and advantageously for at least 10 days, in an amount corresponding to the absorption of at least $10^7$, preferably at least $10^8$, generally between $10^9$ and $10^{12}$, *L. casei* cells.

The present invention will be more clearly understood with the aid of the further description which will follow, which refers to nonlimiting examples illustrating the properties of a *Lactobacillus casei* strain for reinforcing the specific response to microbial antigens.

EXAMPLE 1

Action of *Lactobacillus casei* on T-Cell Proliferation in Response to Antigenic Stimulation A double-blind study versus placebo was carried out in order to test the effect of ingesting a fermented dairy product comprising the *Lactobacillus casei* strain DN-114 001 (CNCM I-1518) on T-cell proliferation in response to antigenic stimulation.

The conditions for this study are as follows:

Individuals 88 healthy individuals, 18 to 50 years old, were recruited in the Department of Infectious Diseases, Washington Hospital Center (Washington D.C.). Individuals with a history of hepatitis or of renal problems, of cardiovascular dysfunctions, of immune or gastro-intestinal diseases, of severe asthma or of sugar diabetes, individuals having undergone treatment with antibiotics or immunosuppressors less than 3 months before the beginning of the study, individuals having a history of alcohol abuse or dependency, individuals with known intolerance or hypersensitivity to dairy products, individuals on a low-calorie diet, individuals having been vaccinated against the flu during the preceding season, and also pregnant women or women who were breastfeeding, were excluded from the study.

The protocol and the conditions of the study were approved by the Research Committee of the WHC, and also by the Institutional Review Board which controls studies carried out in humans.

The individuals selected were randomly divided up into 2 groups:

A group of 47 individuals (26 women and 21 men) received 100 ml per day of a fermented dairy product containing 2% fat, comprising yogurt ferments (*L. bulgaricus* and *S. thermophilus*) and the *Lactobacillus casei* strain DN-114 001, and marketed by DANONE under the trademark ACTIMEL.

A group of 41 individuals (22 women and 19 men) received a placebo for 28 days: 100 ml per day of milk diluted with water (1/5, v/v) supplemented with sugar to give it a calorific value equivalent to that of the ACTIMEL.

The individuals of the 2 groups were asked to refrain from consuming yogurt or other fermented dairy products for the duration of the study.

The mean (standard deviation indicated between parentheses) age of the individuals was 36 (7.3) and 32.7 (7.4), respectively, for the ACTIMEL group and the placebo group.

A blood sample (55 ml) was taken from each individual of the 2 groups before the start of consumption of ACTIMEL or of placebo, in order to determine the base values. The individuals were given control visits on days 9, 18 and 28, and completed a short questionnaire regarding their health, the possible side effects, and also the development of any illness possibly interfering with the interpretation of the results. A blood sample was taken during each visit for the purpose of immunological experiments.

For each individual blood sample, a complete blood cell count and a blood chemistry analysis were performed. In addition, a phenotypic analysis of the leukocytes and of the sub-groups thereof (T cells and sub-groups, B cells, monocytes and NK cells) was performed by flow cytometry.

Measurement of Cell Proliferation

The proliferative response of the T cells of the individuals of the ACTIMEL group and of the individuals of the placebo group, with respect to the three microbial antigens: *candida*, tetanus and influenza, was determined ex vivo by measuring $^3$HTdR incorporation as described below.

Preparation of Cells:

30 ml of heparinized blood from each of the samples taken were treated as follows: the tube was centrifuged for 10 min at 1500 rpm. The plasma was carefully transferred into labeled cryotubes and stored at 70° C. [sic]. The blood was transferred into a 15 ml centrifuge tube and diluted to 1:3 with PBS. 10 ml of Ficoll-hypaque were added to a 50 ml centrifuge tube and covered with 30 ml of the diluted blood. The tube was centrifuged for 2 min at 2000 rpm at ambient temperature. The upper layer of PBS was drawn off and the mononuclear cells were pooled and transferred into a 15 ml centrifuge tube. 10 ml of HBSS were added, vortexed and centrifuged at 1500 rpm for 10 min; the supernatant was drawn off and the pellet was resuspended in 2-3 ml of HBSS. 8 ml of HBSS were added and the tube was centrifuged at 1500 rpm for 6 min. This protocol was repeated twice and the cells recovered were resuspended in 1-2 ml of PBS and then vortexed. The cells were counted, examining their viability by Trypan Blue exclusion, and the concentration thereof was adjusted to $2 \times 10^8$/ml.

Preparation of Antigens:

Tetanus antigen: the preparation was carried out on the day of the assay. A stock solution was prepared by diluting tetanus toxoid (CONNAUGHT LABORATORY, Willowdale, Canada) to 1:1000 in PBS.

*Candida albicans* antigens: a stock solution was prepared by diluting *Candida albicans* antigens (BAYER CO, Elkert, Ind.) to 1:1000 in PBS.

Influenza antigens: a stock solution was prepared by diluting a preparation of influenza virus antigens (NIBSC, Herts, England) to 1:125 in PBS.

Microtitration plates (96 wells) were used. Each well received 100 μl of antigen stock solution and 100 μl of cells at a final concentration of $2 \times 10^5$ cells per well Control wells received 100 μl of PBS instead of the antigen stock solution. The plates were incubated at 37° C., 5% $CO_2$ for 5 days; 18 hours before the end of incubation, 20 μl of 50 μCi/ml $^3$HTdR (NEW ENGLAND NUCLEAR, Boston, Mass.) were added. The cells from the wells of each plate were harvested on filters and these filters were counted directly in a MATRIX 9600 beta-counter (PACKARD INSTRUMENTS) in order to measure the $^3$HTdR incorporation, which is expressed in CPM (counts per minute).

For each individual of the group having received ACTIMEL and for each individual of the group having received the placebo, the proliferation is evaluated by determining the stimulation index (SI) according to the following formula:

$$SI := \frac{\text{mean CPM stimulated cells}}{\text{mean CPM unstimulated cells(control well)}}$$

Statistical Analysis

Descriptive statistics (mean, standard deviation, median) were used to summarize the proliferative response of the T cells to exposure to each antigen, for each of the groups of the study at each measurement time. Due to the distribution bias of the proliferative response, transformation to natural logarithm was used for the proliferation data.

The variations in the proliferative response compared to the base value were used for the statistical modeling [LITTELL et al. SAS System for Mixed Model. North Carolina: SAS Institute Inc, (1996)]. The modifications in proliferative response compared to the base value, as a function of time, were represented using the curve smoothing technique as described by DIGGLE et al. [Analysis of Longitudinal Data. New York: University Press Inc, 1994].

A mixed linear model was developed to study the trajectory of the proliferative response. This model allows adjustment of the proliferation data to a quadratic curve for each group of the study.

This model is defined by the following equation:

$$Y_{ijt} = \alpha_{ij} + \beta 1_j T + \beta 2_j T^2 + \epsilon_{ijt}, \quad i=1,\ldots,n, \; j=1, 2, \; t=1, 2, 3, 4$$

in which:

Yijt denotes the variation in the proliferative response compared to the base value for the individual i in the product group j at time t; transformation to natural logarithm having been applied to each variable, Yijt=Log (proliferation at time t)−Log (base value);

αij denotes the interception for the individual i in the product group j. It reflects a random effect in the model. $\alpha_{ij} \sim$MVN (0, G), G contains the components of the variance in diagonal structure (MVN: multinormal variable distribution);

$\beta 1_j$ and $\beta 2_j$ are the regression coefficients of T and T$^2$ for the product group j;

T is the moment of measurement (day 0, 9, 18 or 28) and T$^2$ is the quadratic term of T.

$\epsilon_{ijt}$ is the error coefficient:

$\epsilon$ijt~MVN (0, R) and R=$\sigma^2 I_n$, in which $I_n$ denotes the identity matrix n×n.

Statistical tests for the following hypotheses were performed:

a) Test whether the estimated regression coefficient is 0.

H$_0$: $\beta 1_j$=0 vs. H$_1$: $\beta 1_j \neq$0 (for a linear term) and H$_0$: $\beta 2_j$=0 vs. H$_1$: $\beta 2_j \neq$0 (for a quadratic term)

If $\beta 1_j$ and $\beta 2_j$ are not different from 0, there is no trajectory.

If $\beta 2_j$ is significantly different from 0, there is a quadratic trajectory.

If only $\beta 1_j$ is significantly different from 0, there is a linear trajectory.

b) Compare whether the trajectories of the two groups are identical.

H$_0$: $\beta 1_1 = \beta 1_2$ vs. H$_1$: $\beta 1_1 \neq \beta 1_2$ (for a linear term) and H$_0$: $\beta 2_1 = \beta 2_2$ vs. H$_1$: $\beta 2_1 \neq \beta 2_2$ (for a quadratic term).

The SAS statistical package was used to carry out the analyses.

Results

Table I below gives the demographic data regarding the individuals and the evaluation of the base value for proliferation.

TABLE I

| Demographic data and base values | | Placebo | ACTIMEL | Placebo vs. ACTIMEL comparison |
|---|---|---|---|---|
| Sex | Female | 22 | 26 | Chi-squared test P = 0.826 |
|  | Male | 19 | 21 |  |
| Age | Mean (SD) | 32.7 (7.4) | 36.0 ± 7.3 | T-test |
|  | Median | 31 | 37 | P = 0.038 |
| Ethnicity | White | 26 | 25 | Chi-squared test Exact p-value = 0.652 |
|  | Black | 12 | 17 |  |
|  | Other | 3 | 5 |  |
| Leukocytes | Mean (SD) | 5997 (1451) | 5810 (1399) | T-test P = 0.540 |
|  | Median | 5992 | 5990 |  |
| Lymphocytes | Mean (SD) | 1932 (567) | 2009 (554) | T-test |
|  | Median | 1812 | 1993 | P = 0.519 |
| CD3$^+$CD4$^+$ | Mean (SD) | 865 (327) | 907 (325) | T-test |
|  | Median | 740 | 818 | P = 0.546 |
| CD3$^+$CD8$^+$ | Mean (SD) | 469 (205) | 431 (181) | T-test |
|  | Median | 417 | 403 | P = 0.360 |
| CD3$^+$CD25$^+$ | Mean (SD) | 380 (200) | 408 (182) | T-test |
|  | Median | 349 | 392 | P = 0.489 |
| CD3$^+$CD45$^+$ | Mean (SD) | 1384 (488) | 1411 (434) | T-test |
|  | Median | 1354 | 1382 | P = 0.783 |

SD = standard deviation

T-Cell Proliferation in Response to Specific Microbial Antigens

The means, standard deviations and medians of the ex vivo proliferation of the peripheral blood mononuclear cells (PBMCs) for each group (ACTIMEL and placebo), at the various sampling times, are given in Table 2 below.

TABLE 2

| | Placebo | | | | ACTIMEL | | | |
|---|---|---|---|---|---|---|---|---|
| Antigen | Day 0 | Day 9 | Day 18 | Day 28 | Day 0 | Day 9 | Day 18 | Day 28 |
| Candida | | | | | | | | |
| Mean | 2.3 | 2.7 | 2.9 | 1.9 | 3.0 | 3.2 | 4.3 | 2.3 |
| SD | 2.0 | 3.1 | 4.1 | 1.2 | 3.4 | 3.5 | 5.6 | 2.6 |
| Median | 1.5 | 1.7 | 1.6 | 1.6 | 1.7 | 1.7 | 2.0 | 1.4 |
| Tetanus | | | | | | | | |
| Mean | 7.3 | 11.8 | 7.9 | 8.7 | 8.4 | 8.7 | 10.3 | 7.8 |
| SD | 7.8 | 12.3 | 8.0 | 8.1 | 15.8 | 10.4 | 11.8 | 8.2 |
| Median | 5.2 | 6.3 | 5.1 | 6.7 | 3.5 | 5.2 | 5.0 | 5.1 |
| Influenza | | | | | | | | |
| Mean | 14.2 | 21.7 | 17.0 | 17.3 | 13.0 | 19.7 | 20.3 | 13.9 |
| SD | 11.4 | 19.1 | 19.6 | 15.7 | 12.6 | 17.1 | 16.6 | 12.7 |
| Median | 11.1 | 16.5 | 9.8 | 12.0 | 9.6 | 16.9 | 17.0 | 11.0 |

SD = standard deviation

There are no significant differences between the two groups of the study for the base values (day 0) for the proliferative response with respect to the three microbial antigens.

FIG. 1 illustrates the variations in the proliferative response over time for each antigen for the two groups of the study: ACTIMEL group: continuous line; placebo group: broken line.

The results of the statistical modeling are provided in Table 3 below.

TABLE 3

| Antigen | Variable | | Parameter estimation | Standard error | $H_0$ test: parameter = 0 | Comparison of the 2 curves |
|---|---|---|---|---|---|---|
| Candida | Placebo | T | 0.017 | 0.014 | P = 0.232 | $H_0$: $\beta1_1 = \beta1_2$ |
| | | $T^2$ | −0.0007 | 0.0005 | P = 0.208 | P = 0.540 |
| | ACTIMEL | T | 0.028 | 0.013 | P = 0.030 | $H_0$: $\beta2_1 = \beta2_2$ |
| | | $T^2$ | −0.0012 | 0.0005 | P = 0.013 | P = 0.458 |
| Tetanus | Placebo | T | 0.034 | 0.014 | P = 0.022 | $H_0$: $\beta1_1 = \beta1_2$ |
| | | $T^2$ | −0.0008 | 0.0005 | P = 0.141 | P = 0.630 |
| | ACTIMEL | T | 0.043 | 0.013 | P = 0.001 | $H_0$: $\beta2_1 = \beta2_2$ |
| | | $T^2$ | −0.0011 | 0.0005 | P = 0.020 | P = 0.626 |
| Influenza | Placebo | T | 0.022 | 0.017 | P = 0.181 | $H_0$: $\beta1_1 = \beta1_2$ |
| | | $T^2$ | −0.0004 | 0.0006 | P = 0.475 | P = 0.045 |
| | ACTIMEL | T | 0.068 | 0.015 | P = 0.0001 | $H_0$: $\beta2_1 = \beta2_2$ |
| | | $T^2$ | −0.0023 | 0.0006 | P = 0.0001 | P = 0.027 |

*Candida:*

In the ACTIMEL group, the base response 3.0±3.4 at day 0 increases to 3.2±3.5 at day 9, and 4.3±5.6 at day 18, and then falls to 2.3±2.6 at day 28 (Table 2). The coefficients estimated for the linear term T and the quadratic term $T^2$ are 0.028 and 0.0012, respectively (Table 3). The two values are statistically significantly different from 0 (p=0.030 and 0.013, respectively). These observations imply that there is a significant positive tendency for the variation in proliferative response to the *Candida* antigen. The proliferative response first increases and then decreases, as shown in FIG. 1a.

The placebo group shows a small change over the period of the study. The regression coefficients estimated for T and $T^2$ are 0.017 and 0.0007. These values are not significantly different from 0 (p=0.232 and 0.208, respectively). These observations indicate that there is no significant change in the proliferative response for the period of the study in the control group. As shown in FIG. 1a, the curve for the placebo group is flatter than the curve for the ACTIMEL group. Although the ACTIMEL group shows a significant trajectory, in contrary to the placebo group, the difference between the two curves does not reach the level of statistical significance (p=0.540 for T and p=0.458 for $T^2$, Table 3).

Tetanus:

For the ACTIMEL group, the response gradually increased from the base level up to day 18, and then fell. The regression coefficients estimated for T and $T^2$ are 0.043 and 0.0011, respectively (Table 3). These two values are significantly different from 0 (p=0.001 and 0.020, respectively). As in the case of *Candida*, the positive variation in proliferative response over the period of the study is significant for the ACTIMEL group. In the placebo group, the mean value increased from 7.3 at day 0 to 11.8 at day 9, then fell to 7.9 at day 18, and increased again to 8.7 at day 28 (FIG. 1b). Even with a non-significant coefficient for the second degree term, $T^2$ (−0.0008, p=0.141, Table 3), the significant estimated coefficient of T (0.034, p=0.022, Table 3) shows a trajectory effect. However, if the ACTIMEL group is compared with the placebo group, the statistical tests do not show any significant differences between the two curves (p=0.630 and 0.626 for T and $T^2$, respectively).

Flu:

The ACTIMEL group showed a clearer change than the placebo group. The mean value increased from 13±12.6 at day 0 to 19.7±17.1 at day 9, remained at this level to day 18, and fell to 13.9±12.7 at day 28 (FIG. 1c). The two coefficients estimated for T and $T^2$ are significantly different from zero (p=0.001). These statistics indicate that the positive change in proliferative response during the period of the study is significant (Table 2).

The placebo group showed variations similar to those observed for tetanus. The mean values increased to day 9, fell to day 18, and increased again to day 28 as illustrated in FIG. 1c. The two estimated regression coefficients are not significantly different from 0 (the p values are 0.181 and 0.475 for T and $T^2$, respectively), indicating that there is no significant trajectory of variations in proliferative response to the influenza antigen.

When the parameters estimated for the ACTIMEL group and the placebo group are compared, significant differences are observed, both for the linear parameters and for the quadratic parameters (p=0.045 for T and p=0.027 for T2) (Table 3). These conclusions indicate that the variations in proliferative response are significantly different between the two groups of the study.

EXAMPLE 2

Action of *Lactobacillus casei* on the Proliferation of T Lymphocyte Subsets in Response to Stimulation with the Influenza Antigen The exact nature of the T subset(s) which respond(s) in vitro to microbial antigens is not known. Either each one of the specific subsets of T lymphocytes, such as those represented by the phenotypes CD3+CD4+, CD3+CD8+, CD3+CD25+, and CD3+CD45+, may be considered to be a primary responder, or these combined subsets may contribute to the total proliferative response to booster antigens.

Presupposing that specific lymphocyte subsets are the main responders to booster antigens, analyses using the statistical model described in Example 1 above were carried out for the T-cell subsets $CD3^+CD4^+$, $CD3^+CD8^+$, $CD3^+CD25^+$, and $CD3^+CD45^+$, in order to determine whether the proliferative response obtained for each of the 4 subsets differed significantly between the ACTIMEL group and the placebo group.

In these analyses, the values for the proliferative response initially based on the total PBMCs were converted, for each subset, into new values calculated according to the total frequency of CD3+CD4+, CD3+CD8+, CD3+CD25+, and CD3+CD45+ T cells in each blood sample. Next, statistical analyses were performed for each subset, as described in Example 1 above.

The means, standard deviations and medians of each of the placebo and ACTIMEL groups, for the four lymphocyte subsets, are given in Table 4 below.

TABLE 4

| Lymphocyte subset | Placebo | | | | ACTIMEL | | | |
|---|---|---|---|---|---|---|---|---|
| | Day 0 | Day 9 | Day 18 | Day 28 | Day 0 | Day 9 | Day 18 | Day 28 |
| CD3 + CD4 + | | | | | | | | |
| Mean | 101 | 149 | 113 | 125 | 87.4 | 131 | 133 | 107 |
| SD | 84.0 | 130 | 117 | 127 | 104 | 90.2 | 112 | 127 |
| Median | 72.8 | 111 | 74.5 | 91.0 | 63.0 | 103 | 92.0 | 64.5 |
| CD3 + CD8 + | | | | | | | | |
| Mean | 192 | 268 | 251 | 251 | 230 | 301 | 365 | 244 |
| SD | 155 | 250 | 289 | 336 | 375 | 286 | 554 | 302 |
| Median | 167 | 218 | 140.5 | 168 | 105 | 180 | 214 | 126 |
| CD3 + CD25 + | | | | | | | | |
| Mean | 250 | 377 | 260 | 354 | 177 | 267 | 310 | 270 |
| SD | 219 | 374 | 208 | 462 | 139 | 163 | 210 | 305 |
| Median | 185 | 263 | 228 | 247 | 159 | 262 | 251 | 177 |
| CD3 + CD45 + | | | | | | | | |
| Mean | 63.5 | 87.6 | 73.0 | 76.2 | 52.1 | 78.7 | 87.1 | 69.1 |
| SD | 54.1 | 70.9 | 81.3 | 79.7 | 72.2 | 56.3 | 79.2 | 95.2 |
| Median | 47.5 | 66.6 | 43.1 | 51.4 | 34.0 | 64.0 | 67.8 | 41.0 |

SD = standard deviation

The differences in the base values between the two groups of the study are not statistically significant.

Figure 2:
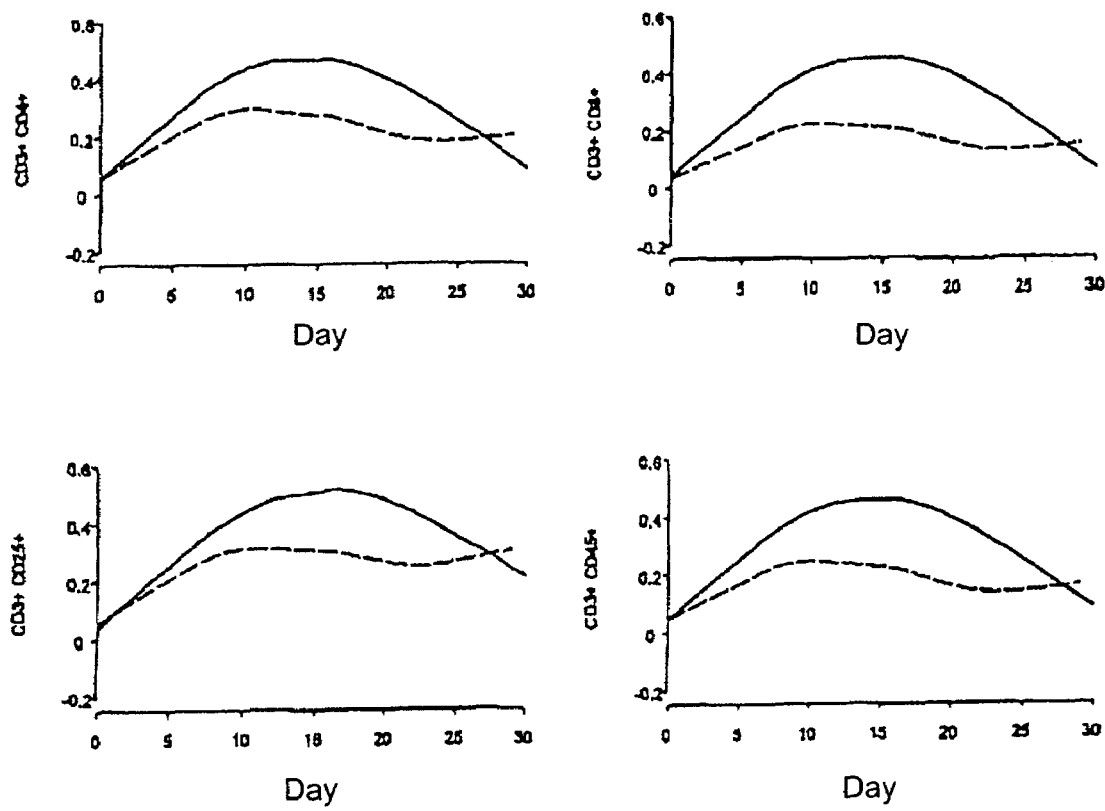
FIG. 2 illustrates the variations in proliferation on algorithmic scale for each lymphocyte subset.

Using the statistical model described in Example 1 above, the variations in proliferation relative to these base values, in response to the influenza antigen, were analyzed for each of the four lymphocyte subsets. FIG. 2 illustrates the variations in proliferation, on a logarithmic scale, for each of these subsets and for each of the two groups of the study.

The results of the statistical modeling are given in Table 5 below.

The proliferative responses for each of the four lymphocyte subsets are in agreement with those observed for the total PBMCs. During exposure to the influenza antigen, significant variations are observed in the ACTIMEL group for the four lymphocyte subsets. These variations can be represented as a quadratic function of time.

Small variations were observed for the four subsets in the placebo group.

In addition, the differences between the two groups were significant for all the lymphocyte subsets.

CONCLUSION

These results show, for the 3 antigens tested, an increase in the proliferative response induced by an antigen booster, which was greater in the ACTIMEL group than in the placebo group. In the case of the influenza antigen, the increase in the ACTIMEL group is statistically significant compared to that observed in the placebo group, both for the total PBMCs and for each of the T cell subsets CD3+CD4+, CD3+CD8+, CD3+CD25+ and CD3+CD45+.

It therefore appears that the consumption of ACTIMEL induced, in the individuals concerned, an immunological priming in vivo, which led to an ex vivo response of their T cells to the microbial antigens, and in particular to the influenza antigens, which was better than that observed in the placebo group.

This increase in the response correlates with the frequency and the status of activation of the $CD3^+$ T cells, and of the subsets thereof, in the individuals of the ACTIMEL group.

In addition, the positive correlation with the presence of the CD25 activation marker suggests the involvement of an in vivo activation of influenza-specific T cells expressing CD25 IL-2 receptors and capable of responding more effectively to the influenza antigens. The analysis of the T-cell subsets also suggests that the proliferative response probably involves both the $CD4^+$ and the $CD8^+$ subset corresponding to the influenza antigen. The importance of the $CD3^+/CD8^+$ T subset in the analysis of the proliferation suggests the possibility of in vivo priming of the pool of influenza-specific CD8+ cytotoxic cells.

TABLE 5

| Lymphocyte subset | Variable | | Parameter estimation (SE) | | $H_0$ test: parameter = 0 | Comparison of the 2 curves |
|---|---|---|---|---|---|---|
| CD3 + CD45 + | Placebo | T | 0.015 | (0.016) | P = 0.352 | $H_0: \beta1_1 = \beta1_2$ |
| | | $T^2$ | −0.0003 | (0.0006) | P = 0.597 | P = 0.015 |
| | ACTIMEL | T | 0.071 | (0.015) | P < 0.001 | $H_0: \beta2_1 = \beta2_2$ |
| | | $T^2$ | −0.0024 | (0.0006) | P < 0.001 | P = 0.016 |
| CD3 + CD25 + | Placebo | T | 0.024 | (0.016) | P = 0.144 | $H_0: \beta1_1 = \beta1_2$ |
| | | $T^2$ | −0.0004 | (0.0006) | P = 0.463 | P = 0.031 |
| | ACTIMEL | T | 0.071 | (0.015) | P < 0.001 | $H_0: \beta2_1 = \beta2_2$ |
| | | $T^2$ | −0.0022 | (0.0006) | P < 0.001 | P = 0.030 |
| CD3 + CD8 + | Placebo | T | 0.014 | (0.017) | P = 0.410 | $H_0: \beta1_1 = \beta1_2$ |
| | | $T^2$ | −0.0003 | (0.0006) | P = 0.671 | P = 0.013 |
| | ACTIMEL | T | 0.070 | (0.015) | P < 0.001 | $H_0: \beta2_1 = \beta2_2$ |
| | | $T^2$ | −0.0024 | (0.0006) | P < 0.001 | P = 0.012 |
| CD3 + CD4 + | Placebo | T | 0.022 | (0.017) | P = 0.203 | $H_0: \beta1_1 = \beta1_2$ |
| | | $T^2$ | −0.0005 | (0.0006) | P = 0.436 | P = 0.028 |
| | ACTIMEL | T | 0.072 | (0.015) | P < 0.001 | $H_0: \beta2_1 = \beta2_2$ |
| | | $T^2$ | −0.0025 | (0.0006) | P < 0.001 | P = 0.024 |

SE = standard error

The invention claimed is:

1. A method for increasing a T cell immune response to an influenza virus comprising:

orally administering to an adult human a composition comprising *Lactobacillus casei* (*L. casei*) strain CNCM I-1518 and a pharmaceutically acceptable diluent or carrier, wherein the composition is administered in an amount effective for increasing a T cell immune response to an influenza virus.

2. The method of claim 1, comprising orally administering the composition for at least one week.

3. The method of claim 1, wherein the composition comprises whole bacteria of the species *L. casei*.

4. The method of claim 1, wherein the composition comprises a bacterial lysate of *L. casei*.

5. The method of claim 1, wherein the composition comprises at least $10^5$ *L. casei* cells per ml.

6. The method of claim 1, wherein the composition comprises at least $10^6$ *L. casei* cells per ml.

7. The method of claim 1, wherein the composition comprises between $1 \times 10^8$ and $1.5 \times 10^9$ *L. casei* cells per ml.

8. The method of claim 1, wherein said composition is in the form of a food or a food supplement.

9. The method of claim 1, wherein said composition is in the form of a fermented dairy product.

10. The method of claim 1, wherein the composition further comprises a yogurt ferment containing *Lactobacillus bulgaricus* and *Streptococcus thermophilus*.

11. The method of claim 10, wherein said yogurt ferment comprises at least $10^7$ *S. thermophilus* cells per ml and at least $5 \times 10^5$ *L. bulgaricus* cells per ml.

12. The method of claim 1, wherein said subject is an adult human who has not been vaccinated against influenza (flu) during the preceding season.

\* \* \* \* \*